(12) United States Patent
Carl

(10) Patent No.: US 7,084,981 B2
(45) Date of Patent: Aug. 1, 2006

(54) METHOD FOR DETERMINING THE PAPER QUALITY FOR HALFTONE PRINTING

(75) Inventor: Gerd Carl, Simmerath (DE)

(73) Assignee: Nordland Papier GmbH, Dorpen (DE)

( * ) Notice: Subject to any disclaimer, the term of this patent is extended or adjusted under 35 U.S.C. 154(b) by 401 days.

(21) Appl. No.: 10/479,404

(22) PCT Filed: Jul. 5, 2002

(86) PCT No.: PCT/EP02/07503

§ 371 (c)(1),
(2), (4) Date: Dec. 2, 2003

(87) PCT Pub. No.: WO03/005004

PCT Pub. Date: Jan. 16, 2003

(65) Prior Publication Data

US 2004/0169864 A1    Sep. 2, 2004

(30) Foreign Application Priority Data

Jul. 6, 2001    (EP)    .................................. 01116410

(51) Int. Cl.
G01N 21/47    (2006.01)
G01N 21/55    (2006.01)
G01B 11/30    (2006.01)
G01N 21/86    (2006.01)

(52) U.S. Cl. .................. 356/446; 356/445; 356/600; 250/559.01

(58) Field of Classification Search ......... 356/445–446
See application file for complete search history.

(56) References Cited

U.S. PATENT DOCUMENTS

| 4,541,273 | A | | 9/1985 | Bery |
| 5,146,097 | A | * | 9/1992 | Fujiwara et al. ............ 250/372 |
| 6,153,038 | A | | 11/2000 | Brooker |

FOREIGN PATENT DOCUMENTS

| JP | 06286325 A | 10/1994 |
| WO | WO 00/39749 | 7/2000 |
| WO | WO 03/005004 A1 | 1/2003 |

* cited by examiner

*Primary Examiner*—Hwa (Andrew) Lee
*Assistant Examiner*—Amanda Merlino
(74) *Attorney, Agent, or Firm*—Alix, Yale & Ristas, LLP

(57) ABSTRACT

The invention relates to a method for determining the paper quality for halftone printing, according to which a finely distributed pattern of geometric figures is applied to the paper, said paper is then illuminated and the light that is reflected and scattered by the paper is observed. The method is characterized in that the pattern is applied to an optical transparent planar element, the side of said element bearing the pattern is brought into contact with the surface of the paper and the paper is pressed against the planar element.

20 Claims, 3 Drawing Sheets

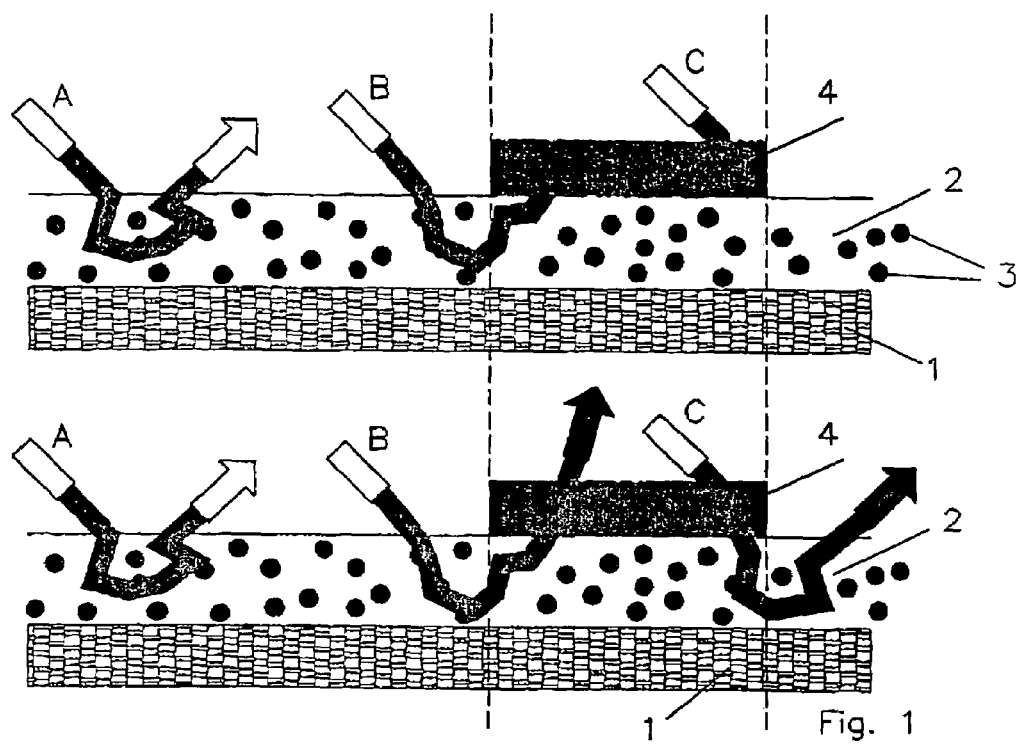
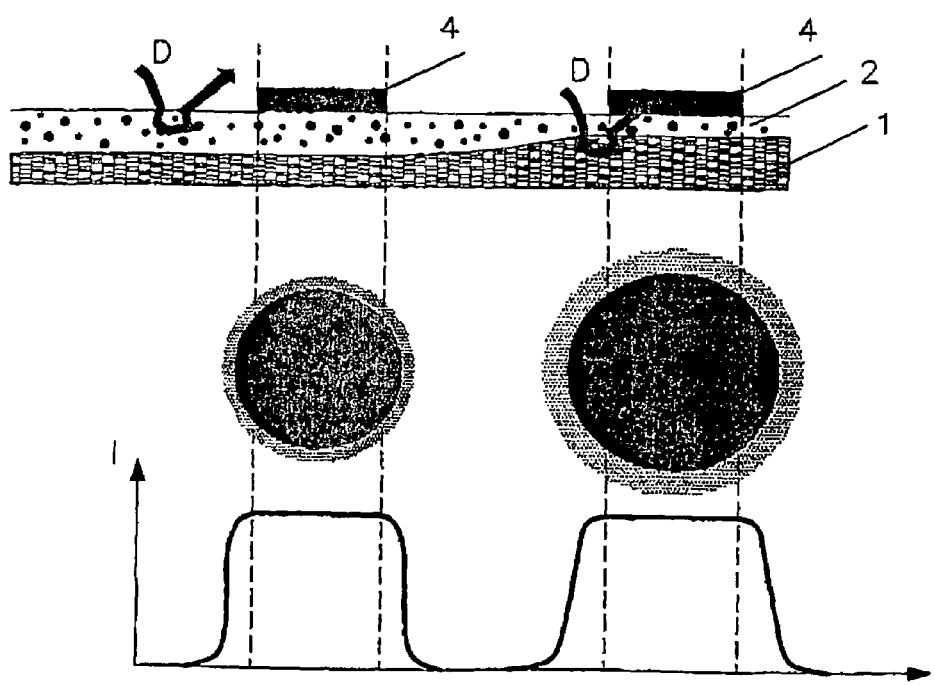
Fig. 1
Fig. 2

METHOD FOR DETERMINING THE PAPER QUALITY FOR HALFTONE PRINTING

BACKGROUND OF THE INVENTION

The invention relates to a method of determining the paper quality for autotypical halftone printing, in which a finely distributed pattern of geometric figures is applied to the paper, the paper is illuminated and the light reflected and scattered by the paper is observed.

During printing, the problem occurs that gray tones can be reproduced only poorly. In order nevertheless to be able to produce prints of good quality with graduated lightness tones, use is therefore made to a widespread extent of the technique of autotypical halftone printing, as it is known. In this case, the image is no longer determined by continuous lightness transition. Instead, the image is built up from a finely distributed pattern of geometric figures, which are normally dots. In a widespread printing technique, these dots are arranged regularly in a grid. Depending on the lightness value at a specific point of the image to be printed, these dots are made larger or smaller. If the points are arranged sufficiently densely and if the printed image is viewed from a sufficient distance, then the individual dots are no longer perceived, but the impression is given of an image with different gray tones or, if dots of different colors are used, of various hues. In certain applications, the dots can also be arranged irregularly, the spacing or the number of dots determining which gray tones or hues are perceived by the observer.

The size of such a dot can be calculated in accordance with the lightness of the image point. At the same time, it is necessary to take account of the fact that the dot will in practice assume a greater area or the printed image perceived by the eye will be more influenced than would have to be the case in theory. One problem in printing technology, which depends on the paper quality of the printing technology and other factors, consists in the fact that, during printing, the dot becomes physically larger than is intended. In particular in the case of prints of high quality, it is of course necessary to take this into account. For such prints, use is normally made of coated paper in which, by means of appropriate surface configuration, it is ensured that the dot does not become significantly larger during printing than is intended. Here, another problem of the apparent enlargement of the dot occurs. The coating is not completely opaque. Instead, the light penetrates into the coating down to a certain depth and into the color layer lying underneath and is then scattered back. The light scattered back does not always reach the eye of the observer, however. If a light beam penetrates under an oblique angle into the coating very close to the edge of a dot, it can be scattered under the dot and no longer emerge from the paper. Light beams which enter close to the dot therefore to some extent do not emerge from the coating again, so that the dot appears larger than it actually is; the edge becomes "blurred", and exhibits a shadow (which is referred to as halation).

There are mathematical models relating to how this dot gain can be determined (Dissertation "Dot Gain in Colour Halftones" by Stefan Gustavson, Linköping, September 1997). This actual or apparent enlargement of the dots can be taken into account on the basis of this mathematical model or else on the basis of optical observation of the finished print, so that theoretically satisfactory prints can be produced. However, this is a purely theoretical conclusion. This cannot be implemented technically, since no printed dots matched appropriately to the respective location can be produced.

However, it has been shown that the optical surface impression of a coated paper is not completely uniform. For example, the paper can have a nonuniform gloss which, of course, leads to a nonuniform intensity of the reflected or scattered light when the print is viewed. The lightness or white color of the coating can be different, which can be caused by a certain blackening, visible fibers of the paper which are not sufficiently covered by the coating and/or a nonuniform distribution of optical whitening agents. The hiding power or opacity of the coating can also be nonuniform, which can be related with the preceding causes, so that light beams penetrate into the paper structure to different depths. In addition, the thickness of the coating can vary locally, which leads to different scatter in the coating and also to nonuniform enlargement of the perceived image of the dot.

All these imperfections of the paper lead to different dot gains. It will be possible to detect these to a more or less greater extent when the print is observed, when the latter has been finished. This is where the present invention starts, it being unsatisfactory, of course, for the deficient quality of the paper to be detected only after the complicated production of the print. In particular, of course a paper manufacturer cannot apply such prints intermediately for test purposes in the reels of paper supplied by him.

The object of the invention consists in providing a method of the type mentioned at the beginning with which the quality of the paper can be determined simply and reliably before printing and without such a print.

SUMMARY OF THE INVENTION

The solution according to the invention is that the pattern is provided on an optically transparent surface element, the latter is brought flat into contact with the paper with the side on which the pattern is located, and the paper is pressed against the surface element.

A determination of the paper quality is therefore carried out without a print having to be made. Although, in theory, the aforementioned dissertation by Gustavson has proposed imaging a screen onto the paper and observing the light scattered back through the screen, in order thereby to determine the apparent enlargement of the dots, the screen does not touch the paper in this case. Here, as the author himself admits, these are purely theoretical considerations which have not been checked experimentally. It is necessary to ask here how the effect of a light beam diffusing under a colored dot and therefore no longer to be observed is to be simulated if no single light beam which emerges from the coating again is actually absorbed at the surface of this coating. In addition, this theoretically proposed method is not used to determine the quality of paper, in particular quality fluctuations, but for checking mathematical models of the aforementioned apparent enlargement of the dots. The dissertation also mentions a method in which a film, on which the appropriate dots are produced, is laid on the paper. However, according to the statements of the author of the aforementioned dissertation, this method, with which the dot gain is again to be examined, suffers from the fact that surface reflections occur which are not present in a normal print, which falsifies the result. In addition, this method was obviously used only for the theoretical examination of the dot gain mechanism, not for determining the paper quality.

A similar method is described in the intermediate report relating to the AiF research project No. 12395N from the Paper Making Institute at the Technical University of Darmstadt. There too, however, the intention is merely to examine light scattering and absorption of the paper on the image reproduction of printed halftone areas, that is to say to examine and check the above effects. The fact that the paper quality, in particular also nonuniformities in the paper quality which would have a highly detrimental effect on the print can therefore also be examined cannot be gathered from the citation. The examination by the University of Darmstadt relates to the general effect of the light trapping phenomenon, while our invention measures the variation and makes it visible. The research project is used for the first practical research into the mathematical models relating to general optical properties of various raw materials.

According to the invention, it has now been found that, even without the proof prints previously necessary, the paper quality can be determined in a quite simple way before printing. The problems with the film laid on in the prior art because of reflections at additional surfaces do not occur or have no influence, since in the case of completely uniform photographic film or the like, the reflection conditions are the same everywhere. Since no absolute values for the dot gains are to be determined, the method operates satisfactorily, simply and accurately in spite of the prejudices mentioned in the dissertation. It is suspected that the problems of the prior art do not occur either in the method according to the invention because the paper is pressed very uniformly against the optically transparent surface element.

The pattern on this optically transparent surface element is uniform. If the paper quality is different over the region of this surface element, differences in the lightness or, in the case of colored dots, possibly also in the color will be detected by eye immediately. In this way, faults in the paper will be detected significantly better than if an image is printed on it which intrinsically already has different lightness graduations and is influenced by the dot transfer of the printing process.

The invention therefore provides, in a surprisingly simple way, a very accurate and sensitive method of checking the paper quality before printing. The method can be applied not only in the case of the coated paper but also in the case of machine-finished paper.

The paper can be pressed against the transparent surface element by a resilient pressing element. In another advantageous embodiment, the paper is pressed against the transparent surface element by means of a diaphragm to which a pressure difference is applied. Here, the pressure difference can be effected by a compressed gas source and/or vacuum.

The transparent surface element can be substantially flat. Here, individual sheets can then be laid on the surface element and examined, or the apparatus can be brought into contact with different points on a paper web, in order to determine the paper quality there. In a particularly advantageous embodiment, however, the transparent surface element is a transparent rotating roll, in which one or more light sources and light-sensitive elements are arranged, and the paper is pressed against the transparent roll by a further roll with a resilient surface. In this case, the scattered light is observed by CCD elements, which can of course also be used in the substantially flat transparent surface elements. The arrangement with the transparent rotating roll makes it possible, firstly, to monitor a moving paper web continuously during production. To this end, it is not necessary for the whole of the paper web to examined but, for example, only a strip about 5 cm wide, since in this way the cylinder does not give rise to any particularly high costs. Since the paper quality is in particular a function of the stock composition, information about the entire width of the paper can be obtained indirectly by means of the measurement in a relatively small strip. In this case, the diameter of the transparent rotating roll is expediently less than the width, since otherwise the roll could run unstably at high speeds. However, the transparent rotating roll can also be used to examine individual sheets in a manner similar to that in a fax machine with original feed.

It is important that the dots are pressed firmly against the paper and there is no spacing between dots and paper, since otherwise radiation would pass under the dots.

It has proven to be particularly expedient for the geometric figures, that is to say in general the dots, to cover approximately 15–70% of the entire viewing area, in particular approximately 20–50% of this viewing area. In this way, particularly sharply formed contrasts are obtained even in the case of small differences in the paper or coating quality. The geometric figures are expediently black, since then lightness differences can be seen particularly clearly. If, instead, geometric figures, in particular dots of different colors, are used, then the image will also exhibit color shadows in the event of fluctuating paper or coating quality.

As already mentioned, in the case of autotypical halftone printing it is possible to arrange the points irregularly, the spacing of these dots determining the lightness value, possibly together with the dot size. For the method according to the invention, however, it is particularly expedient if the dots are screened regularly. It has proven to be particularly expedient if approximately 40 to 100 geometric figures, that is to say points or lines of dots, are provided per centimeter.

In an advantageous embodiment, the transparent surface element is a film or a photographic film, which can be provided particularly simply with the grid of geometric figures or dots. This film or the photographic film is then supported by a transparent glass or plastic plate (or the transparent roll) if the paper is pressed against the film by the vacuum and the diaphragm (or by the resilient roll).

The observation of the different likeness graduations in the event of changing coating or paper quality can be carried out by eye. However, it has proven to be particularly expedient if the observation is carried out by a CCD camera and the image from the same is analyzed electronically.

It is not only possible for the paper from continuous production to be monitored by the method according to the invention. Instead, it is also possible to determine how the quality of the paper improves or becomes worse when production parameters are changed. It is further possible to check how the quality compares with the quality from earlier production runs or with a standard. Testing can be carried out both in the laboratory and in production.

The dots can also be applied without a transparent carrier, for example by Letraset.

BRIEF DESCRIPTION OF THE DRAWINGS

The invention will be described by way of example in the following text using an advantageous embodiment and with reference to the appended drawing, in which:

FIG. 1 shows the scattering of light in coated paper which is printed;

FIG. 2 shows the dot gain with a different thickness of the coating;

DETAILED DESCRIPTION OF THE PREFERRED EMBODIMENT

As FIG. 1 shows, a partly translucent coating 2 which, for example, has pigments 3 is applied to a paper substrate 1 composed of fibers. Light beams A, B and C are scattered differently. In this case, the upper part of FIG. 1 shows a black opaquely printed dot 4, while in the lower part this printed dot 4 is partly transparent to light, like cyan inks, for example. The light beam A is scattered out of the coating 2 in both cases and therefore contributes to the lightness of the image at this point. In the upper illustration with a black printed dot, the light beam B is scattered under this printed dot 4 and therefore cannot leave the coating 2 again. A somewhat blurred, dark region will therefore occur around the printed dot 4, that is to say the dot 4 will appear to be larger than it actually is. It is thereby not only light beams C which fall directly onto the printed dot 4 which are extinguished but also light beams which enter the coating 2 close to the dot 4.

In the lower embodiment of FIG. 1, the light beams which enter the printed dot 4 are not completely extinguished but attenuated. This leads to the light beam B emerging from the dot 4 only in attenuated form, so that the edge of the dot 4 appears darker. On the other hand, the light beam C will emerge from the coating 2, even if attenuated, which also contributes to this dot 4 appearing blurred.

Given different paper qualities or coating qualities, the dot gain will then be different, as illustrated in FIG. 2. In the case of the left-hand dot 4, the light beam D is still scattered out of the coating 2, so that at this point the coating 2 still appears bright when viewed. In the case of the right-hand dot 4, however, the coating 2 is thinner, so that the light beam D is absorbed. The right-hand dot 4 therefore appears to be larger, as illustrated in the lower part of FIG. 2 by the depictions of the dots or the course I of the intensity of the light absorption.

Figure 3:
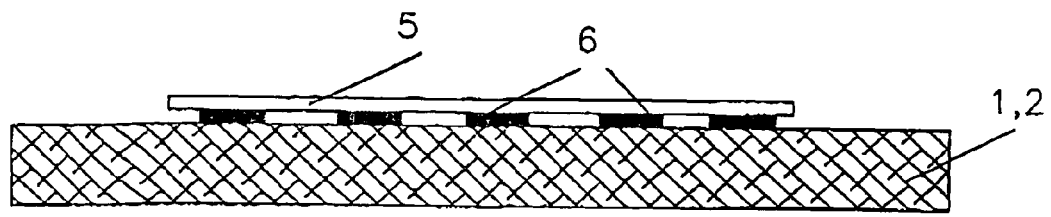
FIG. 3 shows the basic structure of the measuring arrangement in detail.
Figure 4:
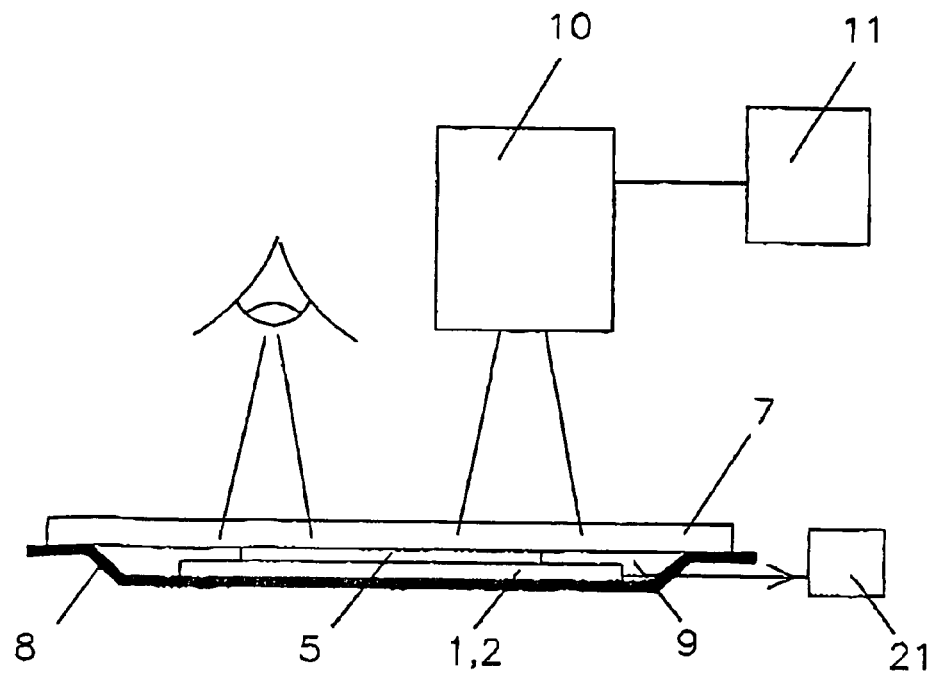
FIG. 4 shows the entire measuring arrangement schematically.

According to the invention, different paper and coating qualities can then be determined by an apparatus which is to be described briefly in conjunction with FIGS. 3 and 4. A film 5, which is provided with dots 6, is applied to the paper 1, 2 (in FIGS. 3 and 4, no distinction is drawn between paper fibers 1 and coating 2). As FIG. 4 shows, this film 5 is supported by a glass plate 7. The paper 1, 2 is laid on that side of the film 5 on which the dots 6 are located, and is pressed against the film 5 by a diaphragm 8, by a vacuum being produced in the space 9 between glass plate 7 and diaphragm 8 by a vacuum pump, also indicated at 21, and said vacuum being maintained. Alternatively, a positive pressure (not shown) could also act externally on the diaphragm 8, or the paper 1, 2 could be pressed against the film by a resilient plunger (not shown). Observation can be carried out by eye, as shown on the left in FIG. 4. Another alternative consists in performing the observation with a CCD camera 10, which then allows electronic evaluation to be performed in a unit 11.

Figure 5:
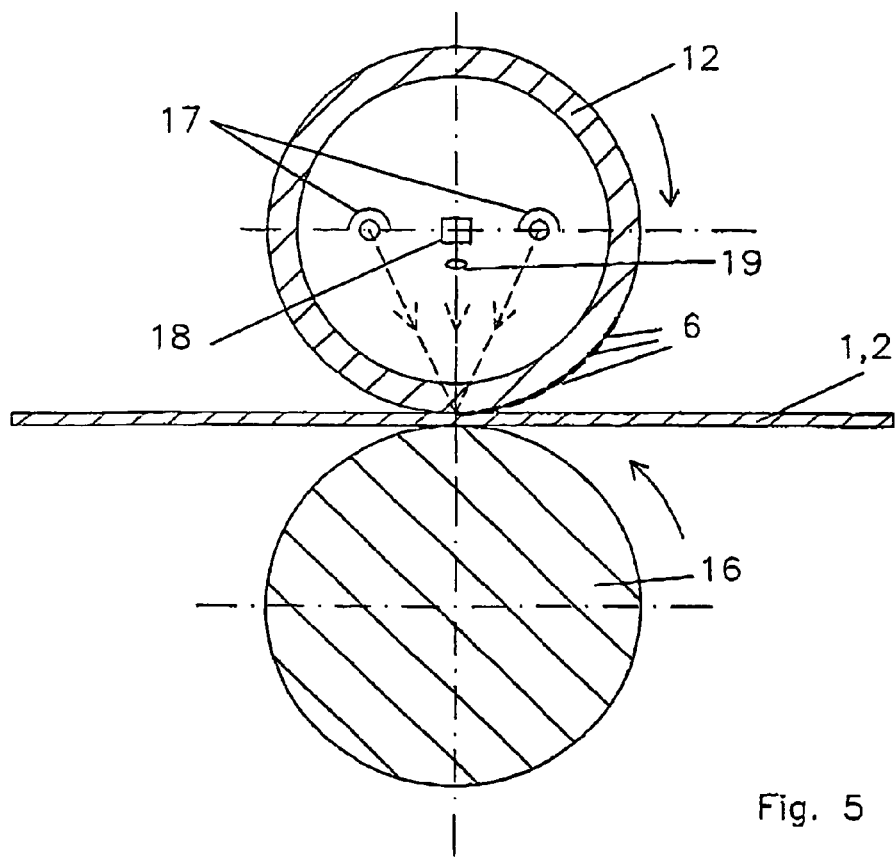
FIG. 5 shows a cross section through the parts essential to the invention and belonging to another apparatus with which the method of the invention can be carried out.
Figure 6:
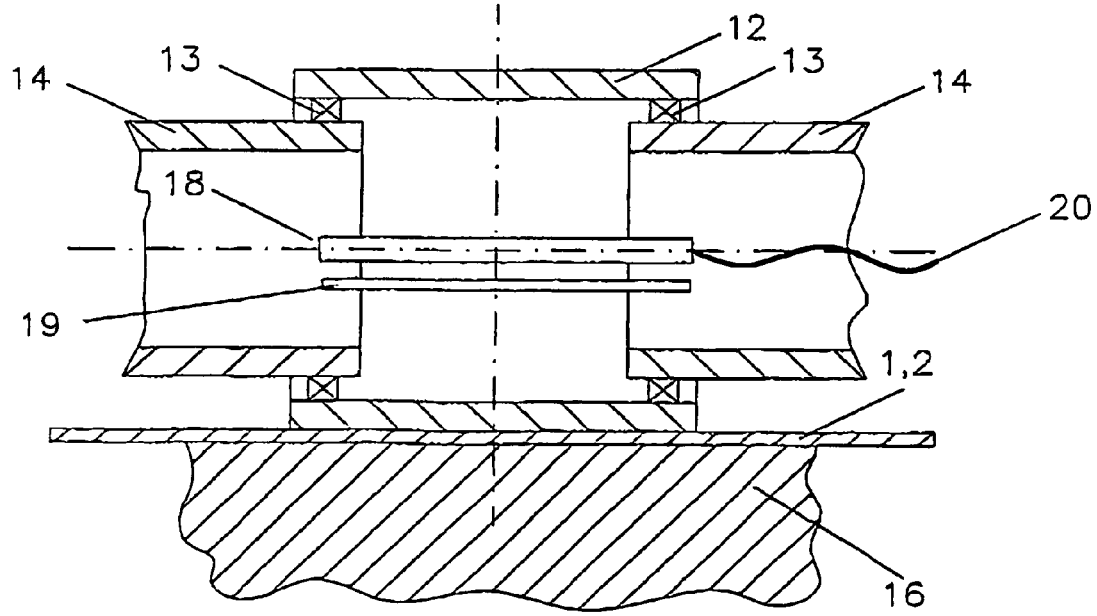
FIG. 6 shows a cross section through parts of the apparatus from FIG. 5.

FIGS. 4 and 5 show an embodiment in which the above-mentioned electronic evaluation is likewise possible. In this case, the surface element is not flat but a hollow roll 12 of transparent material, in particular glass or plastic. As FIG. 6 shows, this roll is mounted by bearings 13 on hollow tubes 14 and can rotate freely. The paper 1, 2 is pressed against the roll 12 by a further roll 16, in particular one made of rubber. The rolls 12 and 16 are either set rotating in the direction of the arrows by the movement of the paper web 1, 2; alternatively the roll 16 can also be driven by a motor, in order for example to draw individual sheets for the examinations into the corresponding apparatus and to draw them between the rolls. Light sources 17 and a row 18 of CCD elements are arranged in the hollow roll 12. The outer surface of the roll 12 is provided with the halftone dots indicated at 6. The light produced by the light sources 17 and illustrated dashed in the fig., which is reflected from the paper web 1, 2 is projected onto the row 18 of CCD elements by projection optics indicated at 19. By means of evaluating the signals from the CCD elements, the paper quality can then be determined, as in the previous embodiment. As FIG. 6 shows, although the roll 12 rotates, the row 18 of CCD elements, the optical projection device 19 and the light sources 17 not shown in FIG. 6 do not rotate at the same time but are fixed to the stationary tubes 14, through which the signals from the row 18 of CCD elements are also led away via the line 20. The supply of power to the light sources 17 is also provided in a similar way.

The invention claimed is:

1. A method of determining the paper quality for autotypical halftone printing, in which a finely distributed pattern of geometric figures is applied to the paper, the paper is illuminated and the light reflected and scattered by the paper is observed, characterized in that the pattern is applied to an optically transparent surface element, which is brought flat into contact with the paper on the side on which the pattern is located, and the paper is pressed against the surface element.

2. The method as claimed in claim 1, characterized in that the geometric figures are dots.

3. The method as claimed in claim 1, characterized in that the paper is pressed against the transparent surface element by a resilient pressing element.

4. The method as claimed in claim 1, characterized in that the paper is pressed against the transparent surface element by a diaphragm to which a pressure difference is applied.

5. The method as claimed in claim 4, characterized in that the pressure difference is effected by a compressed gas source.

6. The method as claimed in claim 4, characterized in that the pressure difference is effected by a vacuum.

7. The method as claimed in claim 1, characterized in that the transparent surface element is a transparent rotating roll in which one or more light sources and light-sensitive elements are arranged, and in that the paper is pressed against the transparent roll by a further roll with a resilient surface.

8. The method as claimed in claim 1, characterized in that the observation of the scattered light is carried out by CCD elements.

9. The method as claimed in claim 1 and wherein the paper has a viewing area, characterized in that the geometric figures cover approximately 15–70% of the total viewing area.

10. The method as claimed in claim 1, characterized in that the geometric figures are black.

11. The method as claimed in claim 1, characterized in that the geometric figures are arranged in a regular grid and approximately 40 to 100 geometric figures or lines of figures are provided per centimeter.

12. The method as claimed in claim 1, characterized in that the transparent surface element has a film which is supported by one of a transparent glass or a plastic plate or a roll.

13. The method as claimed in claim 1, characterized in that the observation is carried out by the human eye.

14. The method as claimed in claim 1, characterized in that the observation is carried out by a CCD camera and the image from the CCD camera is analyzed.

15. The method as claimed in claim 2, characterized in that the dots are applied without a separate transparent carrier.

16. The method as claimed in claim 9, characterized in that the geometric figures cover approximately 20–50% of the total viewing area.

17. The method as claimed in claim 2, characterized in that the paper is pressed against the transparent surface element by a resilient pressing element.

18. The method as claimed in claim 2, characterized in that the paper is pressed against the transparent surface element by a diaphragm to which a pressure difference is applied.

19. The method as claimed in claim 2, characterized in that the transparent surface element is a transparent rotating roll in which one or more light sources and light-sensitive elements are arranged, and in that the paper is pressed against the transparent roll by a further roll with a resilient surface.

20. The method as claimed in claim 12, characterized in that the film is a photographic film.

* * * * *